(12) United States Patent
Leshchiner et al.

(10) Patent No.: US 7,521,434 B2
(45) Date of Patent: Apr. 21, 2009

(54) CROSS-LINKED GELS OF HYALURONIC ACID WITH HYDROPHOBIC POLYMERS AND PROCESSES FOR MAKING THEM

(75) Inventors: Adelya K. Leshchiner, Cresskill, NJ (US); Nancy E. Larsen, Highland Mills, NY (US); Edward G. Parent, North Bergen, NJ (US)

(73) Assignee: Luromed LLC, Tarrytown, NY (US)

( * ) Notice: Subject to any disclaimer, the term of this patent is extended or adjusted under 35 U.S.C. 154(b) by 68 days.

(21) Appl. No.: 11/475,200

(22) Filed: Jun. 27, 2006

(65) Prior Publication Data

US 2006/0293277 A1 Dec. 28, 2006

Related U.S. Application Data

(60) Provisional application No. 60/694,088, filed on Jun. 27, 2005.

(51) Int. Cl.
*A61K 31/728* (2006.01)
*A61K 31/715* (2006.01)
(52) U.S. Cl. ............ 514/54; 514/23; 536/123.1; 536/124
(58) Field of Classification Search .......... 514/54, 514/23; 536/123.1, 124
See application file for complete search history.

(56) References Cited

U.S. PATENT DOCUMENTS 5,633,001 A * 5/1997 .ANG.gerup ............ 424/423

OTHER PUBLICATIONS

Mensitieri et al. (Journal of Material Science: Materials in Medicine (1994), 5(9&10), 743-7).*
Schwarz et al. (Proceedings of the National Academy of Sciences of the United States of America, (May 1973) vol. 70, No. 5, pp. 1608-1612 (Abstract Sent).*

* cited by examiner

*Primary Examiner*—Shaojia Anna Jiang
*Assistant Examiner*—Michael C Henry
(74) *Attorney, Agent, or Firm*—Galvin & Palmer; Sheldon Palmer

(57) ABSTRACT

The present invention provides for compositions of hyaluronic acid cross-linked with at least one other hydrophobic polymer to form a copolymer gel. The preferred composition is a formulation containing hyaluronic acid or its derivatives and a silicone base polymer with a functional group capable of reacting with the preferred cross-linker. The silicon may also be a group capable of undergoing further polymerization, or a silicone moiety adding to the hydrophobic nature of the gel. The product can be used alone or contain various other substances or covalently bound substances for numerous useful applications including cosmetic, medical, and drug delivery applications. The present invention also provides processes for preparing them.

35 Claims, No Drawings

CROSS-LINKED GELS OF HYALURONIC ACID WITH HYDROPHOBIC POLYMERS AND PROCESSES FOR MAKING THEM

CROSS-REFERENCE TO RELATED APPLICATIONS

This is a non-provisional application based on and claiming the benefit of the filing date of provisional application Ser. No. 60/694,088; filed Jun. 27, 2005.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

REFERENCE TO A MICROFICHE APPENDIX

Not Applicable

BACKGROUND OF THE INVENTION

1. Field of the Invention

The present invention relates to compositions of mixed hyaluronic acid ("HA") copolymer gels containing at least one silicone base polymer, formulations containing them, and a method of preparation.

2. Description of the Related Art

Zhao, et al., U.S. Pat. No. 6,703,444 discloses cross-linked HA derivatives, wherein the HA is cross-linked with one or more polymers other than HA having two or more functional groups capable of being covalently bonded with HA to form a product having at least two chemically distinct covalent cross-links between HA and the said polymers. Balazs, et al., U.S. Pat. No. 4,582,865 describes the preparation of cross-linked gels of HA by cross-linking HA by itself or with other hydrophilic polymers using divinyl sulfone as the cross-linking agent.

By way of background, it should be noted that hyaluronic acid (HA) and its derivatives are important materials used in the medical and cosmetic industries. Its unique viscoelastic properties combined with its high water binding properties and exceptional biocompatibility have led to a wide variety of products in the ophthalmic, arthritis, wound healing, antiadhesion, drug delivery, soft tissue augmentation, burn management, and topical cosmetic moisturization fields. Cross-linking of HA has long been used to improve the physical properties of the molecule and to enhance the properties for various uses, or to immobilize the HA to various supports for medical purposes including the diagnosis of male infertility. Formulations of HA have been used in the cosmetic industry as skin moisturizers. Since HA and its salts have similar properties we will refer to them interchangeably as hyaluronic acid or HA. HA is a naturally occurring polysaccharide consisting of alternating N-acetyl-D-glucosamine and D-glucuronic acid monosaccharide units linked with alternating β1-3 glucoronidic and β1-4 glucosaminidic bonds. The molecular weight of hyaluronic acid is generally within the range of 50,000 up to more than 8,000,000. HA is found in all vertebrates in large quantities in the skin, vitreous humor, the synovium, the cartilage, and the umbilical cord. It is not species specific and is therefore highly biocompatible. It is known for its efficiency of hydration, it has a binding capacity of up to 20 times its weight in water; it is the natural moisturizer in the cell matrix of the skin; and it exists at concentrations of 200 microgms per gm of dermal tissue.

BRIEF SUMMARY OF THE INVENTION

In one aspect thereof, the present invention provides cross-linked gels of hyaluronic acid and one or more silicone containing copolymers.

In another aspect, the invention provides mixed cross-linked gels of hyaluronic acid, silicone containing copolymers and at least one other hydrophilic polymer copolymerizable therewith.

In yet another aspect, the invention provides cross-linked gels of hyaluronic acid/silicone containing copolymers and other hydrophobic polymers copolymerizable therewith.

In a still further aspect, the invention provides cross-linked gels of hyaluronic acid and silicone containing copolymers containing low molecular weight substances covalently attached to the macromolecules.

In still yet another aspect, the invention provides various formulations containing cross-linked gels of hyaluronic acid and silicone containing copolymer gels.

Finally, the invention also provides methods of preparing the products of the invention and methods of using the products of the invention in tissue augmentation.

DETAILED DESCRIPTION OF THE INVENTION

Hyaluronic acid (HA) and its derivatives are used in the medical and cosmetic industry. It is an excellent biomaterial for a variety of combined uses the medical field due to its viscoelastic and biocompatibility properties. The water binding and hydration properties of hyaluronic acid provide water to the skin. This moisturizing effect is widely used in the cosmetic industry.

Silicones are a very versatile class of compounds used for many applications by the medical and cosmetic industry. Topical uses of silicone have been applied for wound healing, drug delivery, burn treatment and are typically used in cosmetic formulations. Silicones are in general hydrophobic and their moisturizing properties are generally due to a vapor barrier which they form on the skin.

An important use of hyaluronic acid flows from its properties as a drug delivery vehicle.

Various drug and other pharmaceutically active materials have been loaded into hydrogels of HA and its derivatives, however there are limitations in the type of substances loaded based on their chemical nature. Hydrogels composed largely of water have difficulty accepting substances of hydrophobic nature. Some organic solvents used to solublize a hydrophobic substance may tend to dehydrate the hydrogel or precipitate the HA. Some methods have been developed to overcome this problem although there is still difficulty with some substances. Hyaluronic acid is used for delivery of drugs such as diclofenac.

Silicone Gels are also used for delivery purposes in the medical and the cosmetic industry. Their hydrophobic nature makes them excellent vehicles to incorporate hydrophobic substances. Silicone implants are used to deliver contraceptives and other hydrophobic drugs.

The present invention combines both the advantages of hyaluronic acid and silicone gels in that they contain both hydrophobic and hydrophilic polymers. These gels have the ability to incorporate both large volumes of water and hydrophilic substances as well as hydrophobic substances such as capsaicin. This unique property provides for an improved drug delivery vehicle. The nature of the materials also provides hydrogels with a hydrophobic character, making them easier to formulate into cosmetic compositions.

The present invention as set forth in more detail in the examples which follow, relates to the preparation of compositions of cross-linked polysaccharides in the presence of a silicone compound to form a co-polymerized cross-linked gel.

The invention also relates to compositions prepared by the process of incorporating the silicone compound and involves the addition of a silicon polymer containing a functional group capable of reacting with a cross-linker such as divinyl sulfone (DVS), and conducting cross-linking reaction in the presence of the polysaccharide such as hyaluronan (HA).

The invention also relates to compositions of polysaccharide gels prepared with silicon based cross-linkers from the family of vinyl silicones such as vinyl terminated polydimethylsiloxane (DVTS), trivinylsilane, or 1,3-diallyltetramethyldisiloxane. The properties of the cross-linkers are versatile, the polymer length of vinyl terminated poly(dimethylsiloxane) can give a cross-linker MW between 187 and 155,000. The compositions are prepared by conducting the cross-linking reaction in the presence of a polysaccharide such as hyaluronan (HA) to obtain a cross-linked gel. More than one vinyl cross-linker can be used.

The invention also relates to compositions of polysaccharide gels prepared by a platinum catalyzed cross-linking reaction with one or more vinyl silicones such as divinyltetramethyldisloxane with platinum. The compositions are prepared by conducting cross-linking reaction in the presence of the polysaccharide such as hyaluronan (HA) to obtain a cross-linked gel. More than one vinyl silicone can be used.

The invention also relates to compositions prepared by methods of incorporating compounds into a reaction with a cross-linker such as divinyl sulfone (DVS) or vinyl silicone by the use of a solvent based solution, and conducting the cross-linking reaction in the presence of the polysaccharide such as hyaluronan (HA). Difficulties in incorporating hydrophobic compounds in an aqueous reaction can be overcome by using a water-miscible organic solvent in the cross-linking reaction. This results in a more uniform cross-linking reaction. The solvent should be water-miscible and not reactive with or interfere with the cross-linking agent DVS.

The silicon compound incorporated into the gel may also contain a group capable of undergoing further polymerization or reactions with other functional groups, allowing further modification of the gel. More than one silicone can be used and other polymers may also be included in the gel.

The invention relates to compositions of polysaccharide gels prepared by using multiple cross-linkers, such as a combination of both divinyl sulfone and a vinyl silicone to effect a cross-linking reaction in the presence of the polysaccharide such as hyaluronan (HA).

The invention provides materials that can be used alone or with other substances added to them enhance the properties for a particular purposes. These products may be added or covalently bound substances that can be applied for numerous applications including, cosmetic, medical, and drug delivery.

The invention provides materials that have been demonstrated to be more resistant to biological degradation by hyaluronidase, making such materials useful and more stable as implants. HA implants that have limited lives, because of natural mechanisms for the clearance of HA from the body, can be made more resistant to degradation, and the implants will have improved efficacy in devices used for soft tissue augmentation, drug delivery, anti-adhesion, ophthalmic, and anti-arthritis.

The invention also provides topical compositions with a hydrating effect to the skin. Hyaluronic acid provides a high water binding capacity, typically 20 gm of water per gm of hyaluronic acid. Such a composition will provide a high degree of moisturization to the skin. Compositions of hyaluronic acid have been used to promote wound healing and reduce scarring. Silicone gels and semi-occlusive membranes are commercially available for the treatment of keloids and hypertrophic scars. It is believed that silicon membranes create a barrier impermeable to water thereby creating a moisturization effect which reduces scarring.

The invention is based on hyaluronic acid, a naturally occurring polysaccharide in the human body. It is a common constituent in the tissues and is highly biocompatible. Since the molecule is not species specific it is not antigenic and therefore causes no immune response. The normal content of hyaluronic acid in the skin is 0.2 mg/gm of tissue, but since it is confined to the extracellular space, the concentration of the fluid is actually about 2.5 mg/ml. It will therefore be apparent that since the compositions of the invention cause no inflammation or irritation, they are biologically acceptable treatments.

The invention is described in more detail in the following examples.

EXAMPLES

Example 1

In this, and all succeeding examples, the starting HA, or more specifically sodium hyaluronate ("HA") is of microbial origin, derived from viable hemolytical streptococci and has a molecular weight of about 1.93 million. It is available from Optima Specialty Chemical Corp.

0.6 gm of the sodium hyaluronate was mixed for one day with 20 ml of deionized water to give a 30 mg/ml solution. 300 mg of an aminofunctional siloxane polymer obtained from Dow Corning, namely, dimethyl, methyl (aminoethylaminoisobutyl)siloxane [CAS registration # 106842-44-8], viscosity at 25° C.=3500 mm2/s, 0.875% nitrogen) were added to and stirred into the HA solution. 2 ml of 2.2M NaOH were then added to the mixture and stirred for 20 minutes. Then, 127.7 mg of divinylsulfone ("DVS") were stirred into the solution. The weight ratio of polymer/DVS was about 4.7. A strong gel formed in about 15 minutes. The gel was left for one hour and then put into one liter of 0.15M NaCl. The saline was replenished with fresh saline on the next day, followed by a wash in 1 liter of water the next day. The gel was filtered off using a sixty gauge wire mesh. 78.44 gms of a cloudy, elastic and cohesive gel were formed.

Example 2

0.9 gm of sodium hyaluronate was mixed for one day with 22.5 ml of deionized water to give a 40 mg/ml solution. 450 mg of dimethyl, methyl(aminoethylaminoisobutyl)siloxane were added to the HA solution and stirred into the solution. 2 ml of 2.0M NaOH were then added with 4.15 gm of deionized water to the mixture and stirred for 20 minutes. Then, 195 mg of DVS were stirred into the solution. The weight ratio polymer/DVS was about 7.05. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 114.82 gms of a cloudy, elastic and cohesive gel were formed.

Example 3

0.9 gm of sodium hyaluronate was mixed for one day with 22.5 ml of deionized water to give a 40 mg/ml solution. 450 mg of dimethyl, methyl(aminoethylaminoisobutyl)siloxane were added to the HA solution and stirred into the solution. 2 ml of 2.0M NaOH were then added with 4.15 gm of deionized water to the mixture and stirred for 20 minutes. 4 ml of 1 N HCl were stirred into the gel to stop the degradation. The volume was adjusted with 85.87 gm of 0.15M NaCl to give a final volume of 114.82 gms. This material is a non-crosslinked control used for comparison with a sample of the product of Example 2.

Example 4

0.9 gm of sodium hyaluronate was mixed for one day with 22.5 ml of deionized water to give a 40 mg/ml solution. 450 mg of dimethyl, methyl(aminoethylaminoisobutyl)siloxane were added to the HA solution and stirred into the solution. 2 ml of 2.0M NaOH were then added with 4.15 gm of deionized water to the mixture and stirred for 20 minutes. Then, 270 mg of DVS were stirred into the solution. The weight ratio polymer/DVS was about 5.0. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 117.45 gms of a cloudy, elastic and cohesive gel were formed.

Example 5

0.9 gm of sodium hyaluronate was mixed for one day with 22.5 ml of deionized water to give a 40 mg/ml solution. 450 mg of dimethyl, methyl(aminoethylaminoisobutyl)siloxane were added to the HA solution and stirred into the solution. 2 ml of 2.0M NaOH were added with 4.15 gm of deionized water to the mixture and stirred for 20 minutes. 4 ml of 1 N HCL were stirred into the gel to stop the degradation. The volume was adjusted with 87.6 gm of 0.15M NaCl to give a final volume of 117.45 gms. This is a non-crosslinked control used for comparison with a sample of the product of Example 4.

Example 6

0.9 gm of sodium hyaluronate was mixed for one day with 22.5 ml of deionized water to give a 40 mg/ml solution. 450 mg of dimethyl, methyl(aminoethylaminoisobutyl)siloxane were added to the HA solution and stirred into the solution. 3 ml of 2.0M NaOH were then added with 3.929 gm of deionized water to the mixture and stirred for 20 minutes. Then, 135 mg of DVS were stirred into the solution. The weight ratio polymer/DVS was about 10.0. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 132.14 gms of a cloudy, elastic and cohesive gel were formed.

Example 7

0.9 gm of sodium hyaluronate was mixed for one day with 131.69 ml of deionized water and 450 mg of dimethyl, methyl (aminoethylaminoisobutyl)siloxane to give a final volume of 132.14 gms. This is a non-crosslinked control used for comparison with a sample of the product of Example 6.

Example 8

0.675 gm sodium hyaluronate was mixed for one day with 16.875 ml of deionized water to give a 40 mg/ml solution. 675 mg of dimethyl, methyl(aminoethylaminoisobutyl)siloxane were added to the HA solution and stirred into the solution. 3 ml of 2.0M NaOH were then added with 9.279 gm of deionized water to the mixture and stirred for 20 minutes. Then, 195 mg of DVS were stirred into the solution. The weight ratio polymer/DVS was about 7.05. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 108.39 gms of a cloudy, elastic and cohesive gel were formed.

Example 9

0.675 gm sodium hyaluronate was mixed for one day with 16.875 ml of deionized water to give a 40 mg/ml solution. 675 mg of dimethyl, methyl(aminoethylaminoisobutyl)siloxane were added to the HA solution and stirred into the solution. 2 ml of 2.0M NaOH were then added with 9.78 gm of deionized water to the mixture and stirred for 20 minutes. Then, 270 mg of DVS were stirred into the solution. The weight ratio polymer/DVS was about 5.0. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 104.23 gms of a cloudy, elastic and cohesive gel were formed.

Example 10

Viscosity measurements were taken using a Brookfield DV-II+ at several shear rates. Samples treated with the crosslinking agent divinyl sulfone were compared with those not so treated. The viscosities of the samples treated with the cross-linker had consistently higher values at all shear rates measured indicating that crosslinking occurred.

| Shear Rate | Crosslinked Example 2 | Untreated Example 3 | Crosslinked Example 4 | Untreated Example 5 | Crosslinked Example 6 | Untreated Example 7 |
|---|---|---|---|---|---|---|
| .066 | 513000 | 31993 | 605000 | 22395 | 486000 | 30394 |
| .088 | 435000 | 31193 | 489000 | 21595 | 397000 | 29994 |

-continued

| Shear Rate | Crosslinked Example 2 | Untreated Example 3 | Crosslinked Example 4 | Untreated Example 5 | Crosslinked Example 6 | Untreated Example 7 |
|---|---|---|---|---|---|---|
| .132 | 342000 | 28794 | 378000 | 19996 | 299000 | 27194 |
| .176 | 288000 | 27594 | 315000 | 19196 | 246000 | 25794 |

Example 11

The cross-linked HA silicon gel prepared in Example 1 was used to formulate a topical skin treatment. 60 gms of capsaicin were added to 40 gms of the product as prepared in Example 1. The formulation was homogenous, and without phase separation, indicating that the hydrophobic capsaicin was accepted within in the hydrogel.

Example 12

This example illustrates a formulation for a topical skin treatment with the cross-linked HA silicon gel and capsaicin composition prepared in Example 11.

| Part | Ingredient | % by weight |
|---|---|---|
| 1 | HA Silicon Gel + Capsaicin (Ex. 11) | 20.0 |
| 2 | Carbopol ®940 (Noveon) | 0.25 |
|   | HA | 0.05 |
|   | Water | 64.01 |
|   | Hydroxyethylcellulose | 0.08 |
|   | coagulant | 0.01 |
|   | soy protein | 2.00 |
|   | carrot oil | 3.00 |
|   | calendula | 1.00 |
|   | chamomile | 1.00 |
|   | aloe vera | 2.00 |
|   | glucam | 3.00 |
|   | menthol | 2.00 |
|   | fragrance | 1.00 |
|   | dye/orange-red | 0.10 |
| 3 | triethanolamine | 0.50 |

This formulation was prepared in separate steps as follows: Step 1: was prepared by dispersing 0.25 gm of Carbopol 940 in 49.75 gms of water while mixing with an overhead stirrer until fully hydrated. 0.08 gm of hydroxyethylcellulose was mixed with 7.02 gms of water until fully hydrated. 0.01 gm of coagulant was mixed with 0.99 gms of water until fully hydrated. Step 2: To the Carbopol 940 all of the ingredients from parts 1 and 2 were carefully added and mixed until a homogenous mixture was formed. Step 3: Triethanolamine was slowly added while mixing until a smooth gel formed. A smooth, cream resulted that gave, a silky feel on the skin which contained capsaicin, a substance with known medicinal utility.

Example 13

0.9 gm of sodium hyaluronate was mixed for one day with 22.5 ml of deionized water to give a 40 mg/ml solution. 450 mg dimethyl, methyl(aminoethylaminoisobutyl)siloxane were added to the HA solution and stirred into the solution. 2 ml of 2.0 M NaOH with 4.15 gm of deionized water were then added to the mixture and stirred for 20 minutes. Then, 127.7 mg of DVS were stirred into the solution. The weight ratio HA/DVS was about 7.1 A strong gel formed in about 15 minutes. The gel was left for one hour and then put into one liter of 0.15M NaCl. The saline was replenished with fresh saline on the next day, followed by a wash in 1 liter of water the next day. The gel was filtered off using a sixty gauge wire mesh. 68.20 gms of a cloudy, elastic and cohesive gel were formed.

Example 14

0.9 gm of sodium hyaluronate was mixed for one day with 22.5 ml of deionized water to give a 40 mg/ml solution. 450 mg dimethyl, methyl(aminoethylaminoisobutyl)siloxane were added to the HA solution and stirred into the solution. 2 ml of 2.0M NaOH with 4.15 gm of deionized water were then added to the mixture and stirred for 5 minutes. 0.3 gm of poly dimethylsiloxane vinyl terminated, (DVTS), [CAS # 68951-99-5 provided by Gelest, Inc.] was added and stirred for 15 minutes. The weight ratio HA/DVTS was about 3.0 A gel formed in about 30 minutes. The gel was left for one hour and then the pH was reduced to about 11 by adding 10 ml of 2% HCl. 60 ml of 0.15M NaCl were added to wash. The gel was placed into 1 liter of fresh saline on the next day. The saline was removed leaving 48.36 gms of a soft, cloudy, elastic and cohesive gel.

Example 15

0.9 gm of sodium hyaluronate was mixed for one day with 22.5 ml of deionized water to give a 40 mg/ml solution. 450 mg dimethyl, methyl(aminoethylaminoisobutyl)siloxane were added to and stirred into the HA solution. 2 ml of 2.0M NaOH with 4.15 gm of deionized water were then added to the mixture and stirred for 5 minutes. 0.3 gm of 1,3-diallyltetramethyldisiloxane, (DAS), [CAS # 17955-81-6 provided by Gelest, Inc.] was added and stirred for 15 minutes. The weight ratio HA/DAS was about 3.0 A gel formed in about 30 minutes. The gel was left for one hour and then the pH was reduced to about 11 by adding 10 ml of 2% HCl. 60 ml of 0.15M NaCl were added to the wash. The gel was placed into 1 liter of fresh saline on the next day. The saline was removed leaving 42.10 gms of a soft, cloudy, elastic and cohesive gel.

Example 16

0.9 gm of sodium hyaluronate was mixed for one day with 22.5 ml of deionized water to give a 40 mg/ml solution. 450 mg dimethyl, methyl(aminoethylaminoisobutyl)siloxane were added to and stirred into the HA solution. 2 ml of 2.0M NaOH with 4.15 gm of deionized water were then added to the mixture and stirred for 5 minutes. 0.3 gm of DAS was added and stirred for 15 minutes. Subsequently, 127.7 mg of DVS were stirred into the solution. The weight ratio HA/DVS was about 7.1 The weight ratio HA/DVTS was about 3.0 A strong gel formed in about 15 minutes. The gel was left for one hour and then the pH was reduced to about 11 by adding 10 ml of 2% HCl. 60 ml of 0.15M NaCl were added to wash. The gel was placed into 1 liter of fresh saline on the next day. 66.42 gms of a cloudy, elastic and cohesive gel were formed.

Example 17

0.9 gm of sodium hyaluronate was mixed for one day with 22.5 ml of deionized water to give a 40 mg/ml solution. 450 mg dimethyl, methyl(aminoethylaminoisobutyl)siloxane were added to and stirred into the HA solution. 2 ml of 2.0M NaOH with 4.15 gm of deionized water were then added to the mixture and stirred for 5 minutes. 0.3 gm of DAS was added and stirred for 15 minutes. Subsequently 127.7 mg of DVS were stirred into the solution. The weight ratio HA/DVS was about 7.1 The weight ratio HA/DVTS was about 3.0 A strong gel formed in about 15 minutes. The gel was left for one hour and then the pH was reduced to about 11 by adding 10 ml of 2% HCl. 60 ml of 0.15M NaCl were added to wash. The gel was placed into 1 liter of fresh saline on the next day. 65.50 gms of a cloudy, elastic and cohesive gel were formed.

Example 18

Viscosity measurements were taken using a Brookfield DV-II+ at shear rate=0.022. Samples treated with the crosslinking agents divinyl sulfone (DVS), 1,3-diallyltetramethyldisiloxane (DAS), and poly dimethylsiloxane vinyl terminated, (DVTS) were compared. Finished samples WERE equally homogenized on a Silverson shear mixer. Increasing viscosity with the DAS and the DVTS in addition to DVS indicates the contributions of the crosslinkers.

| DVS Ex 13 | DVTS Ex 14 | DAS Ex 15 | DVS + DVTS Ex 16 | DVS + DAS Ex 17 |
|---|---|---|---|---|
| 1230000 | 23995 | 43191 | 1720000 | 1600000. |

Example 19

9.0 gm of sodium hyaluronate were mixed for one day with 225 ml of deionized water to give a 40 mg/ml solution. 4.5 gm of dimethyl, methyl(aminoethylaminoisobutyl)siloxane were stirred into added to the HA solution. 30 ml of 2.0M NaOH and 38 ml of water were then added to the mixture and stirred for 20 minutes. Then, 2.7 gm of DVS were stirred into the solution. The weight ratio polymer/DVS was about 5.0. A strong gel formed in about 15 minutes. The gel was left for one hour and then put into 2.5 liter of water. The water was replenished twice each day for 1 week. The gel was filtered off using a sixty gauge wire mesh. 1243 gms of a cloudy, elastic and cohesive gel were formed.

Example 20

250 gms of the gel made in Example 19 were homogenized on a Silverson shear mixer for 2 minutes with the low-shear-head at 1200 rpm. Four glass vials filled with 20 ml of the gel and placed in an incubator at 37° C. A vial was removed at the appropriate 1, 5, 9, and 12 month time point to monitor changes in appearance, consistency, pH, and the viscosity. The viscosity was measured on a Brookfield DV II+ Pro viscometer, Spindle #25 with a small cup adapter and a shear rate of 0.110 sec-1, at 25° C.

No significant changes in the gel were noted over 1 year. Only a small decrease was noted in the viscosity resulting in a stable gel.

|  | Appearance | Consistency | pH | Viscosity | % Decrease |
|---|---|---|---|---|---|
| Day 0 | cloudy gel | smooth | 7.2 | 222000 | — |
| 1 month | no change | no change | 7.2 | 206000 | 7.2 |
| 5 months | no change | no change | 7.2 | 191000 | 14.0 |
| 9 months | no change | no change | 7.2 | 189000 | 14.9 |
| 12 months | no change | no change | 7.2 | 220000 | 0.9 |

Example 21

200 gms of the gel made in Example 19 were homogenized on a Silverson shear mixer for 2 minutes with the low-shear-head at 1000 rpm. 50 gms were placed into a 100 ml coming bottle and placed into a steam sterilizer at 121° C. (15 psi) for 20 minutes after which the sample was placed into a water bath to cool. The viscosity was measured on a Brookfield DV II+ Pro viscometer, Spindle #25 with a small cup adapter and a shear rate of 0.110 sec-1, at 25° C. A small, 14.8% decrease in the viscosity was noted resulting in a stable, autoclavable gel.

|  | Appearance | Consistency | Viscosity | % Decrease |
|---|---|---|---|---|
| Initial | cloudy gel | smooth | 236000 | — |
| 20 minute exposure | no change | no change | 201000 | 14.8 |

Example 22

0.9 gm of sodium hyaluronate was mixed for one day with 22.5 ml of deionized water to give a 40 mg/ml solution. 3 ml of 2.0M NaOH were then added with 3.879 gm of deionized water to the mixture and stirred for 20 minutes. Then, 195 mg of DVS were stirred into the solution. The weight ratio polymer/DVS was about 7.05. A strong gel formed in about 15 minutes. The gel was left for one hour and then put into two liters of 0.15M NaCl. The saline was replenished with fresh saline twice during the next 3 days, followed by a wash in 2 liters of water. The gel was filtered off using a sixty gauge wire mesh. 110.14 gms of a clear gel were formed.

Example 23

25 gms of a gel prepared as described in example 2 were mixed with 25 gms of phosphate buffer pH 5.5. 25 gms of a gel control without silicone co-polymer, prepared as in example 22 were mixed with 25 gms of phosphate buffer pH 5.5.

The samples were passed through an 18 gauge needle. 15 ml of sample was placed into the small cup adapter of the Brookfield DV II+ Pro viscometer and the temperature maintained at 25° C. for 30 minutes prior to the addition 50 units of testicular hyaluronidase in 1 ml of 0.1M phosphate buffer pH 5.5. The viscosity was monitored for 6 minutes at 30 second intervals at a shear rate of 22.0 sec-1.

The resulting HA—Silicone gel from example 2 demonstrated an increased resistance to the biological activity of hyaluronidase activity in vitro.

| Time-minutes | HA gel Example 22 - viscosity | HA copolymer Example 2 - viscosity | % initial viscosity HA gel | % initial viscosity HA copolymer gel |
|---|---|---|---|---|
| 1 | 422.3 | 763 | 100 | 100 |
| 1.5 | 355.1 | 767.8 | 84 | 101 |
| 2 | 331.1 | 758.2 | 78 | 99 |
| 2.5 | 302.3 | 739 | 72 | 97 |
| 3 | 268.7 | 715 | 64 | 94 |
| 3.5 | 225.6 | 686.3 | 53 | 90 |
| 4 | 192 | 647.9 | 45 | 85 |
| 4.5 | 182.4 | 619.1 | 43 | 81 |
| 5 | 148.8 | 619.1 | 35 | 81 |

Example 24

1.0 gm of sodium hyaluronate was suspended in 10 ml of methanol. 15 ml of distilled water and 2 ml of 0.2M NaOH were added to hydrate the HA. 0.500 ul of 1,3-diallyltetramethyldisiloxane was added and stirred for 2 minutes, an additional 500 ul of DAS was added and stirred fro 5 minutes. The weight ratio DAS/DVS was about 1.10 ml of 50% methanol in water were added and stirring continued. After 30 minutes, 5 ml of 2% HCL were added to reduce the pH and form gel. The product was allowed to set for 1 hour. The gel was rinsed and washed in 100 ml of water. A smooth elastic and cohesive gel was formed.

Example 25

1.0 gm of sodium hyaluronate was suspended in 10 ml of methanol. 15 ml of distilled water and 2 ml of 0.2 M NaOH were added to hydrate the HA. 0.500 ul of DAS was added and stirred for 2 minutes, an additional 500 ul of DAS was added and stirred for 5 minutes. The weight ratio DAS/DVS was about 1.10 ml of 50% methanol in water were added and stirring continued. After 2 hours the gel was slowly bathed with 10 ml of 2% HCL to reduce the pH and form a rubbery membrane around the gel. The membrane can be removed with scissors and maintained separately and dried. The membrane is resorbable in water.

Example 26

0.9 gm of sodium hyaluronate was mixed for one day with 22.5 ml of deionized water to give a 40 mg/ml solution. 1 ml of 2.0M NaOH was then added with 6.9 gm of deionized water to the mixture and stirred for 5 minutes. Then, 300 mg of trivinylsilane were stirred into the solution. The weight ratio polymer/trivinylsilane was about 3.0. A gel formed in about 30 minutes. The gel was left for two hours and then put into 250 ml of 0.15M NaCl. The saline was replenished with fresh saline twice then once during the next day. 56.28 gms of a clear gel were formed.

Example 27

0.8 gm of sodium hyaluronate was mixed for one day with 20 ml of deionized water to give a 40 mg/ml solution. 0.75 ml of 2.0M NaOH was added and stirred for 20 minutes. The sample was placed in the small sample cup of the Brookfield DV II+ Pro viscometer and the temperature maintained at 25° C. Measurements at a shear rate of 0.044 sec-1 were taken. 100 mg of trivinylsilane was stirred into the solution. The weight ratio polymer/trivinylsilane was about 3.2. The viscosity was monitored at the same shear rate. Measurements were taken at 1 minute intervals for 11 minutes. The rapid and steady increase in viscosity demonstrates the progress of the formation of the gel.

| Viscosity before trivinylsilane addition | Time point (minutes) | Viscosity after trivinylsilane addition | Time point (minutes continued) | Viscosity after trivinylsilane addition |
|---|---|---|---|---|
| 224000 | 0 | 274000 | 7 | 1140000 |
|  | 0.5 | 533000 | 7.5 | 1140000 |
|  | 1 | 679000 | 8 | 1150000 |
|  | 1.5 | 773000 | 8.5 | 1160000 |
|  | 2 | 833000 | 9 | 1180000 |
|  | 2.5 | 885000 | 9.5 | 1180000 |
|  | 3 | 924000 | 10 | 1190000 |
|  | 3.5 | 950000 | 10.5 | 1210000 |
|  | 4 | 977000 | 11 | 1230000 |
|  | 4.5 | 1000000 | 11.5 | 1240000 |
|  | 5 | 1030000 | 12 | 1250000 |
|  | 5.5 | 1060000 | 12.5 | 1260000 |
|  | 6 | 1080000 | 13 | 1270000 |
|  | 6.5 | 1110000 | 13.5 | 1280000 |

Example 28

0.9 gm of sodium hyaluronate was mixed for one day with 22.5 ml of deionized water to give a 40 mg/ml solution. 450 mg of dimethyl, methyl(aminoethylaminoisobutyl)siloxane were added to and stirred into the HA solution. 1 ml of 2.0M NaOH was then added with 6.1 gm of deionized water to the mixture and stirred for 20 minutes. Then, 300 mg of trivinylsilane were stirred into the solution. The weight ratio polymer/trivinylsilane was about 4.5. A gel formed in about 30 minutes. The gel was left for two hours and then put into 250 ml of 0.15M NaCl. The saline was replenished several times over a period of two days. The gel was filtered off using a sixty gauge wire mesh. 49.52 gms of a cloudy, elastic and cohesive gel were formed.

The invention claimed is:

1. A method of preparing a cross-linked gel of hyaluronic acid, said method comprising subjecting sodium hyaluronate in a dilute aqueous alkaline solution at a pH of not less than about 9 to a cross-linking reaction with at least one vinyl functionalized silicone compound as the cross-linking agent at about 20° C.

2. A method according to claim 1 wherein the functionalized silicone compound is 1,3-diallyltetramethyldisiloxane, poly(dimethylsiloxane) vinyl terminated, divinyltetramethyldisiloxane, divinylmethylsilane or trivinylsilane.

3. A method according to claim 1 wherein the reaction is effected in the presence of a platinum catalyst.

4. A method according to claim 3 wherein the platinum catalyst is platinum-divinyltetramethyldisiloxane.

5. A method according to claim 4 wherein the effective concentration of the catalyst is from 1 to 100 ppm.

6. A method of preparing a mixed cross-linked gel of hyaluronic acid and at least one other polymer having a functional group capable of reacting with a vinyl functionalized silicone compound, said method comprising subjecting a mixture of sodium hyaluronate and said other polymer in a dilute aqueous alkaline solution at a pH of not less than 9 to a cross-linking reaction with at least one vinyl functionalized silicone compound as the cross-linking agent at about 20° C.

7. A method according to claim 6 wherein the vinyl functionalized silicone compound is 1,3-diallyltetramethyldisiloxane, poly(dimethylsiloxane) vinyl terminated, divinyltetramethyldisloxane, divinylmethylsilane or trivinylsilane.

8. A method according to claim 7 wherein the vinyl functionalized silicone compound is trivinylsilane.

9. A method according to claim 8 wherein the ratio of the sodium hyaluronate to trivinylsilane concentration is from 20:1 to 1:10 by weight.

10. A method according to claim 6 wherein the reaction is effected in the presence of a platinum catalyst.

11. A method according to claim 10 wherein the platinum catalyst is platinum-divinyltetramethyldisiloxane.

12. A method according to claim 10 wherein the effective concentration of the catalyst is from 1 to 100 ppm.

13. A method of preparing a mixed cross-linked gel of hyaluronic acid and at least one other polymer having a functional group capable of reacting with divinyl sulfone, said method comprising subjecting a mixture of sodium hyaluronate and said other polymer in a dilute aqueous alkaline solution at a pH of not less than about 9 to a cross-linking reaction with divinyl sulfone as the cross-linking agent at about 20° C.

14. A method according to claim 13 wherein the ratio of the polymer to divinyl sulfone concentration is from 20:1 to 1:10 by weight.

15. A method of preparing a mixed cross-linked gel of hyaluronic acid and at least one other polymer having a functional group capable of reacting with a vinyl functionalized silicone compound and divinyl sulfone, said method comprising subjecting a mixture of sodium hyaluronate and said other polymer in a dilute aqueous alkaline solution at a pH of not less than about 9 to a cross-linking reaction with a vinyl functionalized silicone compound and divinyl sulfone as a mixture of cross-linking agents at about 20° C.

16. A method according to claim 15 wherein the vinyl functionalized silicone compound is 1,3-diallyltetramethyldisiloxane, poly(dimethylsiloxane) vinyl terminated, divinyltetramethyldisloxane, divinylmethylsilane or trivinylsilane.

17. A method according to claim 16 wherein the reaction is effected in the presence of a platinum catalyst.

18. A method according to claim 17 wherein the platinum catalyst is platinum-divinyltetramethyldisiloxane.

19. A method according to claim 18 wherein the effective concentration of the catalyst is from 1 to 100 ppm.

20. A method according to claim 16 wherein vinyl functionalized silicone compound is divinylmethylsilane.

21. A method according to claim 15 wherein the ratio of the sodium hyaluronate to divinylmethylsilane concentration is from 20:1 to 1:10 by weight.

22. A method according to claim 6 wherein the said other polymer is a silicone polymer selected from the group consisting of dimethyl, methyl (aminoethylaminoisobutyl) siloxane, silanol terminated poly(dimethylsiloxane), aminoethyl aminopropyl methoxysiloxane-dimethylsiloxane.

23. A method according to claim 15 wherein the said other polymer is a silicone polymer selected from the group consisting of dimethyl, methyl (aminoethylaminoisobutyl) siloxane, silanol terminated poly(dimethylsiloxane), aminoethyl aminopropyl methoxysiloxane-dimethylsiloxane.

24. A method according to claim 6 wherein the combined concentration of sodium hyaluronate and the other polymers in the reaction mixture is 1-20% by weight and the sodium hyaluronate comprises from 0.1-99% of the total.

25. A method according to claim 15 wherein the combined concentration of sodium hyaluronate and the other polymers in the reaction mixture is 1-20% by weight and the sodium hyaluronate comprises from 0.1-99% of the total.

26. A method according to claim 22, wherein the silicone polymer, which is not easily miscible with aqueous solutions, but has a functional group capable of reacting with divinyl sulfone, is solubilized by adding to the dilute aqueous alkaline solution, a further suitable solvent capable of solubilizing the silicone polymer.

27. A method according to claim 23, wherein the silicone polymer, which is not easily miscible with aqueous solutions, but has a functional group capable of reacting with divinyl sulfone, is solubilized by adding to the dilute aqueous alkaline solution, a further suitable solvent capable of solubilizing the silicone polymer.

28. A method according to claim 26 wherein the further suitable solvent is selected from the group consisting of alcohols, ketones, dimethyl sulfoxide, dimethylformamide and tetrahydrofuran.

29. A method according to claim 27 wherein the further suitable solvent is selected from the group consisting of alcohols, ketones, dimethyl sulfoxide, dimethylformamide and tetrahydrofuran.

30. A method according to claim 28 wherein the further suitable solvent is methanol.

31. A method according to claim 29 wherein the further suitable solvent is methanol.

32. A cross-linked gel of hyaluronic acid wherein the hyaluronic acid is cross-linked with one or more silicone containing compounds.

33. A gel as claimed in claim 32 and further comprising a substance having pharmaceutically beneficial activity.

34. A gel as claimed in claim 32 and further comprising a hydrophobic substance.

35. A method of effecting tissue augmentation in a mammal in need thereof, said method comprising injecting into a mammal, at a tissue site in need of augmentation, an effective amount of a composition as claimed in claim 32.

* * * * *